(12) United States Patent
Rozzell, Jr. et al.

(10) Patent No.: US 6,830,904 B2
(45) Date of Patent: Dec. 14, 2004

(54) METHODS FOR PRODUCING DIASTEREOMERS OF ISOLEUCINE

(75) Inventors: J. David Rozzell, Jr., Burbank, CA (US); Basil P. Paulson, Los Angeles, CA (US)

(73) Assignee: BioCatalytics, Inc., Pasadena, CA (US)

( * ) Notice: Subject to any disclaimer, the term of this patent is extended or adjusted under 35 U.S.C. 154(b) by 314 days.

(21) Appl. No.: 10/231,990

(22) Filed: Aug. 30, 2002

(65) Prior Publication Data

US 2004/0048342 A1 Mar. 11, 2004

(51) Int. Cl.$^7$ ............................................... C12P 13/04
(52) U.S. Cl. ................................................... 435/106
(58) Field of Search .......................................... 435/106

(56) References Cited

U.S. PATENT DOCUMENTS

| 5,565,344 A | 10/1996 | Nanba et al. |
| 6,310,242 B1 | 10/2001 | Noda et al. |
| 2003/0219879 A1 * | 11/2003 | Rozzell et al. ............... 435/106 |

FOREIGN PATENT DOCUMENTS

EP 0 937 705 A2 8/1999

OTHER PUBLICATIONS

Williams, et al., "Synthesis of D–Alloisoleucine from L–Isoleucine and from (S)–2–Methylbutan–1–ol. Synthesis of Isostatine", *J. Chem. Soc. Perkin Trans. 1*, 1994, pp. 1969–1974, Universitat de Barcelona Barcelona, Spain.

* cited by examiner

*Primary Examiner*—Herbert J. Lilling
(74) *Attorney, Agent, or Firm*—Christie, Parker & Hale, LLP

(57) ABSTRACT

Methods for producing single diastereomers of isoleucine in high stereochemical purity are provided. D-isoleucine is produced by converting (R)-2-methylbutyraldehyde to a diastereomeric mixture of D-isoleucine hydantoin and L-allo-isoleucine hydantoin (5S-[(R)-1-methylpropyl] hydantoin) under conditions whereby no significant racemization of the chiral center in (R)-2-methylbutyraldehyde occurs, followed by contacting said diastereomeric hydantoin mixture with a D-hydantoinase to stereoselectively hydrolyze any D-isoleucine hydantoin in the mixture to the corresponding N-carbamoyl-D-isoleucine, preferably under conditions permitting the simultaneous epimerization of the chiral center at C-5 of the hydantoin. The simultaneous epimerization permits the reaction to be carried out to substantial completion so that the diastereomeric hydantoin mixture is converted to N-carbamoyl-D-isoleucine in high yield. The N-carbamoyl-D-isoleucine is then decarbamoylated to produce D-isoleucine. Similar procedures are used to produce single diastereomers of L-isoleucine, L-allo-isoleucine, and D-allo-isoleucine.

60 Claims, No Drawings

METHODS FOR PRODUCING DIASTEREOMERS OF ISOLEUCINE

FIELD OF THE INVENTION

This invention relates to methods for producing single diastereomers of isoleucine in high stereochemical purity.

BACKGROUND

Unnatural or non-proteinogenic amino acids, which are structural analogs of the naturally-occurring amino acids that are the constituents of proteins, have important applications as pharmaceutical intermediates. For example, the anti-hypertensives ramipril, enalapril, benazapril, and prinivil are all based on L-homophenylalanine; certain second generation pril analogs are synthesized from p-substituted-L-homophenylalanine. Various β-lactam antibiotics use substituted D-phenylglycine side chains, and newer generation antibiotics are based on aminoadipic acid and other UAAs. The unnatural amino acid L-tert-leucine has been used as a precursor in the synthesis of a number of different developmental drugs.

Unnatural amino acids are used almost exclusively as single stereoisomers. Since unnatural amino acids are not natural metabolites, traditional production methods for amino acids based on fermentation cannot generally be used since no metabolic pathways exist for their synthesis. Given the growing importance of unnatural amino acids as pharmaceutical intermediates, various methods have been developed for their enantiomerically pure preparation. Commonly employed methods include resolutions by diastereomeric crystallization, enzymatic resolution of derivatives, and separation by simulated moving bed (SMB) chiral chromatography. These methods can be used to separate racemic mixtures, but the maximum theoretical yield is only 50%.

The amino acid isoleucine poses special problems due to the presence of a second chiral center. Four distinct diastereomers exist for the constitutional carbon skeleton of isoleucine, consisting of two enantiomeric pairs: L-isoleucine, D-isoleucine, L-allo-isoleucine, and D-allo-isoleucine, having the (2S,3S), (2R,3R), (2S,3R), and (2R,3S) absolute configurations, respectively. The naturally-occurring L-isoleucine can be produced by fermentation, taking advantage of the existing metabolic pathway to introduce both chiral centers. Production of the other isoleucine diastereomers is considerably more difficult, however, because metabolic pathways for their production do not exist. Separation of an equimolar mixture of the four diastereomers, which is extremely difficult and costly due to the chemical similarity of the compounds, can produce only a maximum theoretical yield of 25% of any single diastereomer, and in practice it is always much lower. Synthesis of a racemate in which the relative stereochemistry of the two chiral centers is controlled will still only permit a maximum theoretical yield of 50% when the enantiomers are separated.

D-isoleucine, or (2R,3R)-2-amino-3-methylpentanoic acid, D-allo-isoleucine, or (2R,3S)-2-amino-3-methylpentanoic acid, L-allo-isoleucine, or (2S,3R)-2-amino-3-methylpentanoic acid, and L-isoleucine, or (2S,3S)-2-amino-3-methylpentanoic acid all have applications as pharmaceutical intermediates and as chemicals for medical and biochemical research. Various derivatives are also required for the synthesis of peptides and peptide analogs. Thus, an efficient method for preparation of a single diastereomer of D-isoleucine or D- or L-allo-isoleucine in high stereochemical purity would be highly desirable. The present invention is directed toward a method for the preparation of any of the four diastereomers of the isoleucine carbon skeleton in high stereochemical purity.

SUMMARY OF THE INVENTION

The invention is directed to methods for the preparation of any of the four diastereomers of the isoleucine carbon skeleton in high stereochemical purity. In one embodiment as shown in Scheme 1, the invention is directed to a method for producing D-isoleucine comprising converting (R)-2-methylbutyraldehyde to a diastereomeric mixture of D-isoleucine hydantoin (5R-[(R)-1-methylpropyl]hydantoin) and L-allo-isoleucine hydantoin (5S-[(R)-1-methylpropyl]hydantoin) under conditions whereby no significant racemization of the chiral center in (R)-2-methylbutyraldehyde occurs, followed by contacting said diastereomeric hydantoin mixture with a D-hydantoinase to stereoselectively hydrolyze any D-isoleucine hydantoin in the mixture to the corresponding N-carbamoyl-D-isoleucine. Preferably in the claimed method the contacting of the diastereomeric hydantoin mixture with a D-hydantoinase is carried out under conditions permitting the simultaneous epimerization of the chiral center at C-5 of the hydantoin. As discussed further below, the simultaneous epimerization permits the reaction to be carried out to substantial completion so that the diastereomeric hydantoin mixture is converted to N-carbamoyl-D-isoleucine in high yield. The N-carbamoyl-D-isoleucine is then decarbamoylated to produce D-isoleucine.

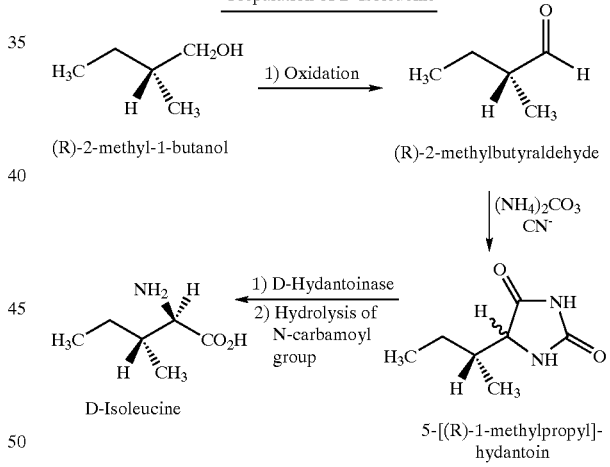

In another embodiment, as shown in Scheme 2, the invention is directed to a method for producing L-allo-isoleucine comprising converting (R)-2-methylbutyraldehyde to a diastereomeric mixture of D-isoleucine hydantoin and L-allo-isoleucine hydantoin under conditions whereby no significant racemization of the chiral center in (R)-2-methylbutyraldehyde occurs, followed by contacting said diastereomeric hydantoin mixture with an L-hydantoinase to stereoselectively hydrolyze any L-allo-isoleucine hydantoin in the mixture to the corresponding N-carbamoyl-L-allo-isoleucine. Preferably in the claimed method the contacting of the diastereomeric hydantoin mixture with an L-hydantoinase is carried out under conditions permitting the simultaneous epimerization of the chiral center at C-5 of the hydantoin. As discussed further below, the simultaneous epimerization permits the reaction to be carried out to substantial completion so that the diastereomeric hydantoin mixture is converted to N-carbamoyl-L-allo-isoleucine in high yield. The N-carbamoyl-L-allo-isoleucine is then decarbamoylated to produce L-allo-isoleucine.

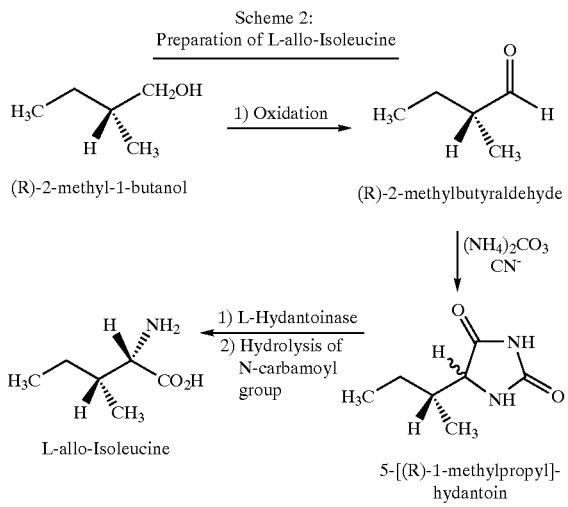

In another embodiment, as shown in Scheme 3, the invention is directed to a method for producing D-allo-isoleucine comprising converting (S)-2-methylbutyraldehyde to a diastereomeric mixture of D-allo-isoleucine hydantoin (5R-[(S)-1-methylpropyl]hydantoin) and L-isoleucine hydantoin (5S-[(S)-1-methylpropyl]hydantoin) under conditions whereby no significant racemization of the chiral center in (S)-2-methylbutyraldehyde occurs, followed by contacting said diastereomeric hydantoin mixture with a D-hydantoinase to stereoselectively hydrolyze any D-allo-isoleucine hydantoin in the mixture to the corresponding N-carbamoyl-D-allo-isoleucine. Preferably in the claimed method the contacting of the diastereomeric hydantoin mixture with a D-hydantoinase is carried out under conditions permitting the simultaneous epimerization of the chiral center at C-5 of the hydantoin. As discussed further below, the simultaneous epimerization permits the reaction to be carried out to substantial completion so that the diastereomeric hydantoin mixture is converted to N-carbamoyl-D-allo-isoleucine in high yield. The N-carbamoyl-D-allo-isoleucine is then decarbamoylated to produce D-allo-isoleucine.

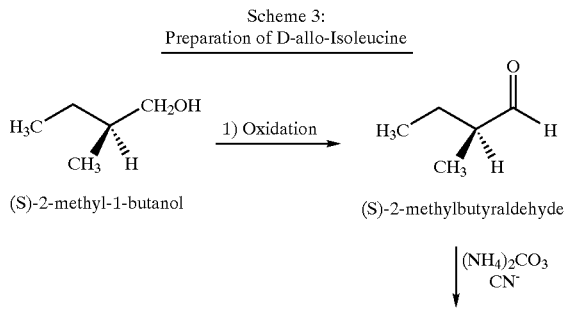

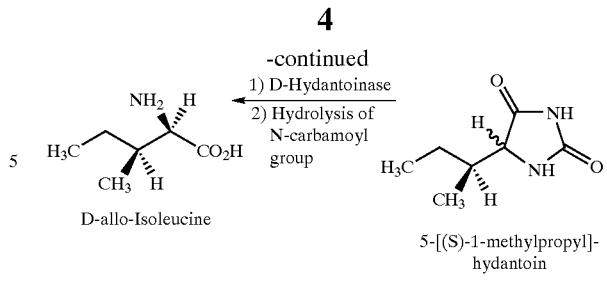

In another embodiment, as shown in Scheme 4, the invention is directed to a method for producing L-isoleucine comprising converting (S)-2-methylbutyraldehyde to a diastereomeric mixture of D-allo-isoleucine hydantoin and L-isoleucine hydantoin under conditions whereby no significant racemization of the chiral center in (S)-2-methylbutyraldehyde occurs, followed by contacting said diastereomeric hydantoin mixture with an L-hydantoinase to stereoselectively hydrolyze any L-isoleucine hydantoin in the mixture to the corresponding N-carbamoyl-L-isoleucine. Preferably in the claimed method the contacting of the diastereomeric hydantoin mixture with an L-hydantoinase is carried out under conditions permitting the simultaneous epimerization of the chiral center at C-5 of the hydantoin. As discussed further below, the simultaneous epimerization permits the reaction to be carried out to substantial completion so that the diastereomeric hydantoin mixture is converted to N-carbamoyl-L-isoleucine in high yield. The N-carbamoyl-L-isoleucine is then decarbamoylated to produce L-isoleucine.

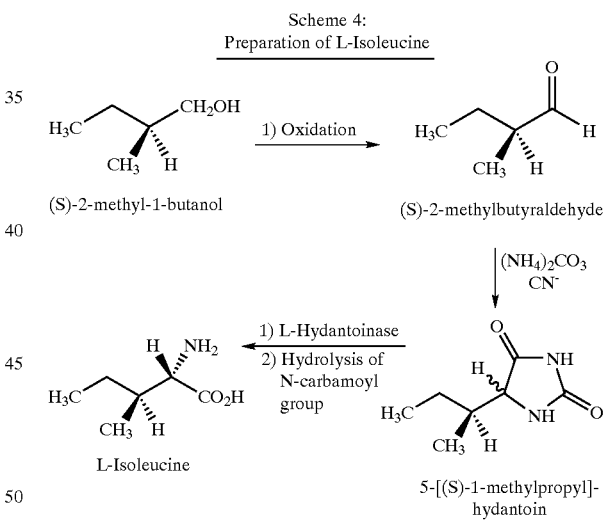

In yet another embodiment, the invention is directed to a method for producing single diastereomers of N-carbamoyl-D-isoleucine. A method for producing N-carbamoyl-D-isoleucine comprises converting (R)-2-methylbutyraldehyde to a diastereomeric mixture of D-isoleucine hydantoin and L-allo-isoleucine hydantoin under conditions whereby no significant racemization of the chiral center in (R)-2-methylbutyraldehyde occurs (Scheme 1 above), followed by contacting said diastereomeric hydantoin mixture with a D-hydantoinase to stereoselectively hydrolyze any D-isoleucine hydantoin in the mixture to the corresponding N-carbamoyl-D-isoleucine. Preferably in the claimed method the contacting of the diastereomeric hydantoin mixture with a D-hydantoinase is carried out under conditions permitting the simultaneous epimerization of the chiral center at C-5 of the hydantoin. As discussed further below, the simultaneous epimerization permits the reaction to be carried out to substantial completion so that the diastereomeric hydantoin mixture is converted to N-carbamoyl-D-isoleucine in high yield.

In another embodiment, the invention is directed to a method for producing N-carbamoyl-L-allo-isoleucine comprising converting (R)-2-methylbutyraldehyde to a diastereomeric mixture of D-isoleucine hydantoin and L-allo-isoleucine hydantoin under conditions whereby no significant racemization of the chiral center in (R)-2-methylbutyraldehyde occurs (Scheme 2 above), followed by contacting said diastereomeric hydantoin mixture with an L-hydantoinase to stereoselectively hydrolyze any L-allo-isoleucine hydantoin in the mixture to the corresponding N-carbamoyl-L-allo-isoleucine. Preferably in the claimed method the contacting of the diastereomeric hydantoin mixture with an L-hydantoinase is carried out under conditions permitting the simultaneous epimerization of the chiral center at C-5 of the hydantoin. As discussed further below, the simultaneous epimerization permits the reaction to be carried out to substantial completion so that the diastereomeric hydantoin mixture is converted to N-carbamoyl-L-allo-isoleucine in high yield.

In another embodiment, the invention is directed to a method for producing N-carbamoyl-D-allo-isoleucine comprising converting (S)-2-methylbutyraldehyde to a diastereomeric mixture of D-allo-isoleucine hydantoin and L-isoleucine hydantoin under conditions whereby no significant racemization of the chiral center in (S)-2-methylbutyraldehyde occurs (Scheme 3 above), followed by contacting said diastereomeric hydantoin mixture with a D-hydantoinase to stereoselectively hydrolyze any D-allo-isoleucine hydantoin in the mixture to the corresponding N-carbamoyl-D-allo-isoleucine. Preferably in the claimed method the contacting of the diastereomeric hydantoin mixture with a D-hydantoinase is carried out under conditions permitting the simultaneous epimerization of the chiral center at C-5 of the hydantoin. As discussed further below, the simultaneous epimerization permits the reaction to be carried out to substantial completion so that the diastereomeric hydantoin mixture is converted to N-carbamoyl-D-allo-isoleucine in high yield.

In another embodiment, the invention is directed to a method for producing N-carbamoyl-L-isoleucine comprising converting (S)-2-methylbutyraldehyde to a diastereomeric mixture of D-allo-isoleucine hydantoin and L-isoleucine hydantoin under conditions whereby no significant racemization of the chiral center in (S)-2-methylbutyraldehyde occurs (Scheme 4 above), followed by contacting said diastereomeric hydantoin mixture with an L-hydantoinase to stereoselectively hydrolyze any L-isoleucine hydantoin in the mixture to the corresponding N-carbamoyl-L-isoleucine. Preferably in the claimed method the contacting of the diastereomeric hydantoin mixture with an L-hydantoinase is carried out under conditions permitting the simultaneous epimerization of the chiral center at C-5 of the hydantoin. As discussed further below, the simultaneous epimerization permits the reaction to be carried out to substantial completion so that the diastereomeric hydantoin mixture is converted to N-carbamoyl-L-isoleucine in high yield.

DETAILED DESCRIPTION

The present invention is directed to methods for the preparation of each of the four diastereomers of isoleucine in high stereochemical purity. The methods of the invention are based on the conversion of single enantiomers of 2-methylbutyraldehyde to isoleucine hydantoins (5-[1-methylpropyl]hydantoin) under conditions in which no significant racemization of the chiral center in 2-methylbutyraldehyde occurs, followed by the use of a stereoselective enzymatic reaction catalyzed by a hydantoinase, in which the aforementioned hydantoin serves as the precursor. By "conditions in which no significant racemization of the chiral center in 2-methylbutyraldehyde occurs" is meant conditions in which the 5-[-methylpropyl]hydantoin is formed from a pure enantiomer of 2-methylbutyraldehyde and in which the racemization at the carbon atom derived from 2-methylbutyraldehyde is less than about 5%, more preferably less than about 2%, and most preferably less than about 1%. For example, in the case of (R)-2-methylbutyraldehyde being converted to 5-[(R)-1-methylpropyl]hydantoin (a mixture of stereoisomers at C-5 of the hydantoin), the amount of 5-[(S)-1-methylpropyl]hydantoin is less than about 5% of the product, preferably less than about 2% of the product, and most preferably less than about 1% of the product. Similarly, in the case of (S)-2-methylbutyraldehyde being converted to 5-[(S)-1-methylpropyl]hydantoin (a mixture of stereoisomers at C-5 of the hydantoin), the amount of 5-[(R)-1-methylpropyl]hydantoin is less than about 5% of the product, preferably less than about 2% of the product, and most preferably less than about 1% of the product.

In the practice of this invention, conditions that cause no significant racemization of the chiral center in 2-methylbutyraldehyde involve reaction of either (R)-2-methylbutyraldehyde or (S)-2-methylbutyraldehyde in aqueous ethanol with, for example, potassium cyanide and ammonium carbonate at moderate temperature. Preferably, the temperature of the reaction is maintained from about 20° C. to about 95° C., and more preferably from about 40° C. to about 90° C. Strongly basic conditions are preferably avoided. In carrying out the reaction, ammonium ion is preferably administered as ammonium carbonate. For example, (R)-2-methylbutyraldehyde can be added to a mixture of 300 mM ammonium carbonate and 75 mM potassium cyanide at a temperature ranging from about 50° C. to about 90° C. When the reaction is complete, the desired 5-[1R-methylpropyl]hydantoin (a mixture of stereoisomers at C-5 of the hydantoin; vide infra) can be recovered as a solid by cooling of the reaction mixture on ice. The hydantoin product can be recovered prior to further reaction, if desired, by crystallization from water or water-alcohol mixtures, by precipitation from the reaction mixture after concentration, by chromatography, or any other suitable method.

The starting chiral aldehyde can be obtained as a single enantiomer by oxidation of enantiomerically-pure 2-methylbutanol using methods known in the art. For example, S-2-methylbutanol (Aldrich Chemical Company, Milwaukee, Wis. USA) is oxidized to (S)-2-methylbutyraldehyde via the Swern oxidation of (S)-2-methyl-1-butanol. In a typical procedure, S-2-methyl-1-butanol is contacted with a mixture of oxalyl chloride and dimethyl sulfoxide in methylene chloride in the presence of triethylamine. Similarly, R-2-methyl-1-butanol can be oxidized to (R)-2-methylbutyraldehyde using the same conditions. Other oxidation methods known in the art may also be used provided that racemization of the enantiomerically pure 2-methylbutyraldehyde does not occur. The single enantiomer of 2-methylbutyraldehyde (either R or S absolute configuration) that is produced contains preferably at least about 95% of the desired enantiomer, more preferably at least about 98% of the desired enantiomer, and still more preferably at least about 99% of the desired enantiomer. The single enantiomers of 2-methyl-1-butanol may be purchased commercially or, if desired, they can be obtained by resolution of racemic 2-methyl-1-butanol by methods well-known to those skilled in the art. For example, racemic 2-methyl-1-butanol can be resolved by stereoselective acylation of the alcohol using a lipase or esterase enzyme and an appropriate acylating agent (see, for example, Bornscheuer, U. T. et al. "Hydrolases in Organic Synthesis: Regio- and Stereoselective Biotransformations", Wiley-VCH, Chapter 4, pp. 44–47, 1999, and Faber, K "Biotransformations in Organic Chemistry: A Textbook" $3^{rd}$ Edition, Springer, Chapter 2, pp. 59–115, 1997, the disclosures of which are incorporated herein by reference. In a representative procedure, 2-methyl-1-butanol is dissolved in vinyl acetate, and lyophilized lipase enzyme is suspended in the solution with stirring. When the reaction is complete, the unreacted 2-methyl-1-butanol is separated as a single stereoisomer from the 2-methyl-1-butyl acetate, for example, by distillation. Other acylating agents and enzymes may also be used provided that the agent or enzyme used catalyzes the stereoselective acylation of predominantly only one of the stereoisomers of 2-methyl-1-butanol.

The hydantoin is then contacted with an enantioselective hydantoinase under conditions permitting the epimerization of the hydantoin at the 5-position. As referred to herein, "enantioselective hydantoinase" means a hydantoinase enzyme that is selective for catalyzing the hydrolysis of only one of the stereoisomers at C-5 of the hydantoin. For example, a D-hydantoinase (or R-hydantoinase) is selective for catalyzing the hydrolysis of a hydantoin possessing the R absolute configuration at C-5 of the hydantoin; similarly, an L-hydantoinase (or S-hydantoinase) is selective for catalyzing the hydrolysis of a hydantoin possessing the S absolute configuration at C-5 of the hydantoin. As referred to herein, "epimerization of the hydantoin at the 5-position" means interconversion of the R and S absolute configurations of the chiral center at C-5 of the hydantoin. In the practice of this invention, one condition useful for epimerization of the hydantoin at the 5-position is maintaining a pH of about 7.5 or higher, preferably 8.0 or higher. Epimerization of the hydantoin at the 5-position may also be achieved by contacting the hydantoin with an appropriate racemase, that is, an enzyme that can catalyze the epimerization at C-5 of the hydantoin. Only the chiral center at C-5 of the hydantoin is racemized under these conditions; the second chiral center in the molecule is unaffected.

When this racemization occurs in the presence of a D-hydantoinase, an equilibrium is established between hydantoins possessing the R and S absolute configurations at C-5 of the hydantoin. For example, an equilibrium would be established between L-isoleucine hydantoin and D-allo-isoleucine hydantoin; similarly an equilibrium would be established between L-allo-isoleucine hydantoin and D-isoleucine hydantoin. When a mixture of L-isoleucine hydantoin and D-allo-isoleucine hydantoin is contacted with a D-hydantoinase, the D-allo-isoleucine hydantoin is selectively hydrolyzed by the D-hydantoinase to form the N-carbamoyl-D-allo-isoleucine. As the D-allo-isoleucine hydantoin is depleted from the mixture by D-hydantoinase-catalyzed hydrolysis, the equilibrium between the L-isoleucine hydantoin and the D-allo-isoleucine hydantoin is re-established under the epimerizing conditions, continuously generating additional D-allo-isoleucine hydantoin for stereoselective hydrolysis by the D-hydantoinase enzyme. This continual supply of the hydantoin of D-allo-isoleucine occurs during the course of the reaction until substantially all of the hydantoin has been converted to N-carbamoyl-D-allo-isoleucine. In this way, the reaction can be carried out to substantial completion. By the term "substantial completion" is meant that at least about 75%, preferably at least about 85%, and more preferably at least about 95%, of the mixture of L-isoleucine hydantoin and D-allo-isoleucine hydantoin is converted to N-carbamoyl-D-allo-isoleucine. The yield of N-carbamoyl-D-allo-isoleucine produced by the method of the present invention can approach 100% of theoretical, given sufficient reaction time and/or sufficient hydantoinase enzyme. Similarly, when a mixture of D-isoleucine hydantoin and L-allo-isoleucine hydantoin is contacted with a D-hydantoinase, the D-isoleucine hydantoin is selectively hydrolyzed by the D-hydantoinase to form the N-carbamoyl-D-isoleucine. As the D-isoleucine hydantoin is depleted from the mixture by D-hydantoinase-catalyzed hydrolysis, the equilibrium between the L-allo-isoleucine hydantoin and the D-isoleucine hydantoin is re-established under the epimerizing conditions, continuously generating additional D-isoleucine hydantoin for stereoselective hydrolysis by the D-hydantoinase enzyme. This continual supply of the hydantoin of D-isoleucine occurs during the course of the reaction until substantially all of the mixture of D-isoleucine hydantoin and L-allo-isoleucine hydantoin has been converted to N-carbamoyl-D-isoleucine. In this way, the reaction can be carried out to substantial completion so that the mixture of D-isoleucine hydantoin and L-allo-isoleucine hydantoin is converted almost completely to N-carbamoyl-D-allo-isoleucine. In similar fashion using an L-hydantoinase, L-allo-isoleucine can be produced from a mixture of D-isoleucine hydantoin and L-allo-isoleucine hydantoin, and L-isoleucine can be produced form a mixture of D-allo-isoleucine hydantoin and L-isoleucine hydantoin.

The reaction can be monitored, if desired, by any suitable method known in the art. An example of a method useful for monitoring the extent of reaction in the D-hydantoinase-catalyzed hydrolysis is thin layer chromatography on silica gel. Alternatively, high performance liquid chromatography can be used to monitor the extent of reaction.

In carrying out the hydantoinase catalyzed conversions of isoleucine hydantoin mixtures, the pH of the reaction mixture is an important factor. The pH is adjusted such that epimerization at C-5 of the hydantoin can occur at a rate that is not too slow, yet the pH is preferably not so high that the hydantoinase enzyme is inactivated. Preferably the pH of the reaction mixture ranges from about 7.5 to about 11.5, more preferably from about 8.0 to about 9.5. The hydantoinase catalyzed conversion to form a single stereoisomer of an N-carbamoyl-isoleucine can be carried out over a wide range of temperatures, depending on the stability and activity of the hydantoinase. Preferably, the reaction is carried out at a temperature ranging from about 10° C. to about 80° C., and more preferably the reaction is carried out at a temperature ranging from about 30° C. to about 75° C.

In carrying out the hydantoinase-catalyzed hydrolysis step, either immobilized or non-immobilized D-hydantoinase or L-hydantoinase can be used. Both immobilized and non-immobilized hydantoinases are commercially available. For example, the immobilized D-hydantoinase product number 1582194, carrier fixed is commercially available from BioCatalytics, Inc., Pasadena, Calif. BioCatalytics, Inc., also sells a non-immobilized D-hydantoinase under the product number D-HYD2. Similarly, any L-hydantoinase that catalyzes the hydrolysis of L-isoleucine hydantoin or L-allo-isoleucine hydantoin can be used in the practice of this invention, immobilized or non-immobilized.

Irrespective of how a D-hydantoinase or L-hydantoinase is discovered or generated, any D-hydantoinase or L-hydantoinase that is capable of hydrolyzing the hydantoin of isoleucine stereoselectively may be used in the practice of this invention. A number of D- and L-hydantoinases useful in the practice of this invention are known in the art. Examples of D-selective hydantoinases that may be used in the invention include D-hydantoinase I and D-hydantoinase II, which are available commercially from BioCatalytics, Inc., (Pasadena, Calif.). The use of these hydantoinases has been described by Keil et al. [Tetrahedron: Asymmetry, vol. 6, pp. 1257–1260 (1995), the disclosure of which is incorporated herein by reference]. A number of other hydantoinases that are useful in the practice of this invention have been described by Syldakt and Wagner in Biocatalytic Production of Amino Acids and Derivatives, Chapter 5, pp. 75–128, D. Rozzell and F. Wagner, eds., Hanser publishers, Munich, 1992, hereby incorporated by reference. L-Hydantoinases are also well-known in the art (see, for example C. Syldatk et al in "Biocatalytic Production of Amino Acids and Derivatives," J. D. Rozzell and F. Wagner, editors, Hanser Publishers, 1992, pp. 129–176, hereby incorporated by reference). Hydantoinases useful in the practice of this invention may also be discovered by screening or developed using various mutagenesis and screening procedures. Such mutagenesis and screening procedures are known in the art by names such as directed evolution, shuffling, molecular breeding, gene reassembly, gene redesign, and the like.

Decarbamoylation of N-carbamoyl-isoleucine can be accomplished either chemically or enzymatically by any suitable method. One chemical method of decarbamoylation useful in the practice of this invention involves the use of nitrous acid. This method has been described by Keil et al. [Tetrahedron: Asymmetry, vol. 6, pp. 1257–1260 (1995)], and references cited therein. Enzymatic methods for decarbamoylation are also known. One method useful in the practice of this invention involves the use of a carbamoylase enzyme. This method has been described generally for other D-amino acids by Nanba et al., U.S. Pat. No. 5,565,344, hereby incorporated by reference.

Following decarbamoylation, the single diastereomer of isoleucine that is produced can be isolated by any suitable method, such as ion exchange chromatography, crystallization from a concentrated aqueous solution or an aqueous/alcohol mixture, or precipitation with ethanol or acetone. Single diastereomers of isoleucine may be isolated as zwitterions, or, if desired, they may also be crystallized as salts. Salts useful for the crystallization of single diastereomers of isoleucine include, but are not limited to, dicyclohexylammonium, dibenzylammonium, diethylammonium, and the like.

The invention will now be described by the following examples, which are presented here for illustrative purposes and are not intended to limit the scope of the invention.

EXAMPLE 1

Synthesis of (S)-2-Methylbutyraldehyde

A 250 ml round bottom flask containing 2.2 ml of oxalyl chloride (25 mmoles) and 16 ml methylene chloride was cooled in a dry ice/acetone bath. The mixture was stirred with a magnetic stirrer and sparged with nitrogen for 10 minutes. A solution containing 3.5 ml dimethyl sulfoxide (50 mmoles) in 11 ml methylene chloride was added drop wise to the flask. After two minutes a solution containing 2.5 ml (S)-2-methyl-1-butanol (23 mmoles) in 7 ml methylene chloride was added to the reaction. The solution was stirred with cooling on a dry ice bath for 15 minutes, at which time 8 ml triethylamine was added. The solution was allowed to warm to room temperature and stirred overnight.

EXAMPLE 2

Conversion of (S)-2-Methylbutyraldehyde to a Mixture of L-Isoleucine Hydantoin and D-Allo-Isoleucine Hydantoin The crude product from the oxidation step in Example 1 was used immediately without further purification. Three hundred twenty-three milliliters of water, 35 milliliters of ethanol, 9.8 grams (100 mmoles) ammonium carbonate, and 1.6 grams (25 mmoles) potassium cyanide were added to the crude oxidation reaction mixture of Example 1. The flask was fit with a condenser, and the solution was warmed to 60° C. and stirred overnight. The condenser was then removed and the mixture was warmed to 85° C. for 2 hours. The crude reaction mixture was then cooled in an ice bath yielding 0.35 g (2.1 mmoles) of a mixture of L-isoleucine hydantoin and D-allo-isoleucine hydantoin. The product was analyzed by HPLC using an Astec Chirobiotic T column (250 mm×4.6 um 30% methanol/water, flow rate: 1.0 ml/min). The analysis of the product showed two peaks for each isomer in a 1:1 ratio. A reference chromatogram of the 5-[1-methylpropyl] hydantoin (a mixture of isoleucine hydantoins) made from racemic 2-methyl-1-butanol indicated that the stereochemistry at the methyl group was retained throughout the reaction sequence and that no significant racemization of 2-methylbutyraldehyde occurred.

EXAMPLE 3

Conversion of a Mixture of L-Isoleucine Hydantoin and D-Allo-Isoleucine Hydantoin to N-Carbamoyl-D-Allo-Isoleucine Using an Immobilized D-Hydantoinase A mixture of L-isoleucine hydantoin and D-allo-isoleucine hydantoin (2 g), prepared as described in Example 2, was suspended in 100 ml of glycine-NaOH buffer (0.1 M, pH=8.5) containing 1 mM of $MnCl_2$ under nitrogen. When the mixture was heated to 50° C., the hydantoin was dissolved. Hydantoinase I (1 g, BioCatalytics, Inc., Pasadena, Calif. USA, catalog number 1582194, carrier fixed) was added, and the mixture was stirred at 50° C. under nitrogen. The pH was controlled at 8.5 by the addition of a 1 N NaOH solution. The reaction was monitored by HPLC [Column: ChrownPack CR(+); eluent: $H_2O$]. After the starting material was consumed (approximately 24 hrs), the mixture was filtered. The analytical yield of N-carbamoyl-D-allo-isoleucine was near 100%. To recover the product, the filtrate was acidified to pH=1 to 2 and maintained at room temperature. The resulting precipitate was separated via filtration and dried to give the product as a colorless solid (1.4 g, 63% yield).

EXAMPLE 4

Alternative Conversion of a Mixture of L-Isoleucine Hydantoin and D-Allo-Isoleucine Hydantoin to N-Carbamoyl-D-Allo-Isoleucine Using a Non-Immobilized D-Hydantoinase A mixture of L-isoleucine hydantoin and D-allo-isoleucine hydantoin (2 g), prepared as described in Example 2, was suspended in 100 ml of glycine-NaOH buffer (0.1 M, pH=9.0) containing 1 mM of $MnCl_2$ under nitrogen. When the mixture was heated to 50° C., the hydantoin was dissolved. Hydantoinase II (0.05 g, BioCatalytics, Inc., Pasadena, Calif. USA, catalog number HYD-2) was added, and the mixture was stirred at 50° C. under nitrogen. The pH was controlled at 9.0 by the addition of a 3 N ammonium hydroxide solution. The reaction was monitored by HPLC [Column: ChrownPack CR(+); eluent: $H_2O$]. After the starting material was consumed (approximately 24 hrs), the mixture was filtered. The filtrate was acidified to pH=1 to 2 and maintained at room temperature. The resulting precipitate was separated via filtration and dried to give the product as a colorless solid (1.5 g, 65% yield).

EXAMPLE 5
Decarbamoylation of N-Carbamoyl-D-Allo-Isoleucine Using a Carbamoylase Enzyme N-carbamoyl-D-allo-isoleucine (50 mg), prepared as described in Example 3, was dissolved in 20 ml of sodium phosphate buffer (0.1 M, pH=8.0) and 20 mg of carbamoylase (BioCatalytics, Inc., Pasadena, Calif. USA, product number DECARB-1) was added to the mixture. The mixture was shaken at 40° C. The reaction was monitored by HPLC [Column: ChrownPack CR(+); eluent: 0.01 M $HClO_4$ solution]. When the reaction was complete, the resulting mixture was deposited on the DOWEX-50 ion exchange column. The column was washed with water and the pure D-allo-isoleucine was eluted with 0.01 N $NH_4OH$ solution and recovered by evaporation in vacuo (31 mg, 82% yield). The optical purity was >99% the single diastereomer of D-allo-isoleucine.

EXAMPLE 6
Alternative Decarbamoylation of N-Carbamoyl-D-Allo-Isoleucine Using a Carbamoylase Enzyme The procedure of Example 5 was repeated except that the pH used was 7.5. D-allo-isoleucine was isolated in 80% yield.

EXAMPLE 7
Alternative Decarbamoylation of N-Carbamoyl-D-Allo-Isoleucine Using Nitrous Acid N-carbamoyl-D-allo-isoleucine (87 mg, 0.5 mmol), prepared as described in Example 2, was suspended in 20 ml of 3.5 N hydrochloric acid. The mixture was cooled to 0° C., and 0.5 mmol of sodium nitrite was added. The reaction was monitored by HPLC [Column: ChrownPack CR(+); eluent: 0.01 M $HClO_4$ solution]. When the conversion was close to 100%, the mixture was neutralized with 4 N NaOH solution. The resulting mixture was deposited on the DOWEX-50 ion exchange column. The column was washed with water, and the pure D-allo-isoleucine was eluted with 0.01 N $NH_4OH$ solution and recovered by evaporation in vacuo (28 mg, 43% yield).

EXAMPLE 8
Alternative Decarbamoylation of N-Carbamoyl-D-Allo-Isoleucine Using Sulfuric Acid N-carbamoyl-D-allo-isoleucine (87 mg, 0.5 mmol), prepared as described in Example 2, was suspended in 20 ml of 6 N sulfuric acid. The mixture was heated to 100° C. and maintained at this temperature until the reaction was complete. The reaction was monitored by HPLC [Column: ChrownPack CR(+); eluent: 0.01 M $HClO_4$ solution]. When the starting material was consumed, the mixture was neutralized by the addition of a solution of 4 N NaOH. The resulting mixture was deposited on the DOWEX-50 ion exchange column. The column was washed with water, and the pure D-allo-isoleucine was eluted with a solution of 0.01 N $NH_4OH$ and recovered by evaporation in vacuo.

EXAMPLE 9
Single-Pot Conversion of a Mixture of L-Isoleucine Hydantoin and D-Allo-Isoleucine Hydantoin to D-Allo-Isoleucine Using a D-Hydantoinase and Decarbamoylase L-isoleucine hydantoin (2 g), prepared as described in Example 1, is suspended in 100 ml of glycine-NaOH buffer (0.1 M, pH=9.0) containing 1 mM of $MnCl_2$ under nitrogen, and the mixture is heated 50° C. Hydantoinase II (0.05 g, BioCatalytics, Inc., Pasadena, Calif. USA, catalog number HYD-2) is added, and the mixture is stirred at 50° C. under nitrogen. The pH is controlled at 9.0 by the addition of a 3 N ammonium hydroxide solution. The progress of the reaction is monitored by HPLC [Column: ChrownPack CR(+); eluent: $H_2O$]. After the hydantoin is completely converted (24 hrs), the pH of the solution is adjusted to 8.0 by the addition of 6 N HCl. Twenty milligrams of carbamoylase (BioCatalytics, Inc., Pasadena, Calif. USA, product number DECARB-1) is added to the mixture. The mixture is stirred at 40° C. and monitored by HPLC [Column: ChrownPack CR(+); eluent: 0.01 M $HClO_4$ solution]. When the reaction is complete, the resulting mixture is deposited on the DOWEX-50 ion exchange column. The column is washed with water and the pure D-allo-isoleucine eluted with 0.01 N $NH_4OH$ solution and recovered by evaporation in vacuo.

EXAMPLE 10
Conversion of a Mixture of L-Isoleucine Hydantoin and D-Allo-Isoleucine Hydantoin to N-Carbamoyl-L-Isoleucine Using an L-Hydantoinase The procedures of either Example 3 or Example 4 are repeated except that an L-hydantoinase is used in place of a D-hydantoinase.

EXAMPLE 11
Decarbamoylation of N-Carbamoyl-L-Isoleucine Using a Carbamoylase Enzyme The procedure of Example 5 is repeated except that N-carbamoyl-L-isoleucine is used in place of N-carbamoyl-D-allo-isoleucine and a carbamoylase enzyme capable of decarbamoylating N-carbamoyl-L-isoleucine is used in place of the DECARB-1 carbamoylase enzyme.

EXAMPLE 12
Alternative Decarbamoylation of N-Carbamoyl-L-Isoleucine Using Nitrous Acid The procedure of Example 7 is repeated except that N-carbamoyl-L-isoleucine, prepared as described in Example 9, is used in place of N-carbamoyl-D-allo-isoleucine.

EXAMPLE 13
Synthesis of (R)-2-Methylbutyraldehyde

The procedure of Example 1 is repeated except that (R)-2-methyl-1-butanol is used in place of (S)-2-methyl-1-butanol.

EXAMPLE 14
Conversion of (R)-2-Methylbutyraldehyde to a Mixture of L-Allo-Isoleucine Hydantoin and D-Isoleucine Hydantoin The procedure of Example 2 is repeated except that (R)-2-methylbutyraldehyde is used in place of (S)-2-methylbutyraldehyde.

EXAMPLE 15
Conversion of a Mixture of L-Allo-Isoleucine Hydantoin and D-Isoleucine Hydantoin to N-Carbamoyl-D-Isoleucine Using an Immobilized D-Hydantoinase The procedure of Example 3 is repeated except that a mixture of L-allo-isoleucine hydantoin and D-isoleucine hydantoin, prepared as described in Example 14, is used in place of a mixture of L-isoleucine hydantoin and D-allo-isoleucine hydantoin.

EXAMPLE 16
Alternative Conversion of a Mixture of L-Allo-Isoleucine Hydantoin and D-Isoleucine Hydantoin to N-Carbamoyl-D-Isoleucine Using a Non-Immobilized D-Hydantoinase The procedure of Example 4 is repeated except that a mixture of L-allo-isoleucine hydantoin and D-isoleucine hydantoin is used in place of a mixture of L-isoleucine hydantoin and D-allo-isoleucine hydantoin.

EXAMPLE 17
Decarbamoylation of N-Carbamoyl-D-Isoleucine Using a Carbamoylase Enzyme The procedure of Example 5 is repeated except that N-carbamoyl-D-isoleucine is used in place of N-carbamoyl-D-allo-isoleucine.

EXAMPLE 18
Alternative Decarbamoylation of N-Carbamoyl-D-Isoleucine Using Nitrous Acid The procedure of Example 7 is repeated except that N-carbamoyl-D-isoleucine is used in place of N-carbamoyl-D-allo-isoleucine.

EXAMPLE 19
Conversion of a Mixture of L-Allo-Isoleucine Hydantoin and D-Isoleucine Hydantoin to N-Carbamoyl-L-Allo-Isoleucine Using an L-Hydantoinase The procedure of Example 10 is repeated except that a mixture of L-allo-isoleucine hydantoin and D-isoleucine hydantoin, produced as described in Example 14, is used in place of a mixture of L-isoleucine hydantoin and D-allo-isoleucine hydantoin.

EXAMPLE 20
Decarbamoylation of N-Carbamoyl-L-Allo-Isoleucine Using a Carbamoylase Enzyme The procedure of Example 11 is repeated except that N-carbamoyl-L-allo-isoleucine is used in place of N-carbamoyl-L-isoleucine.

EXAMPLE 21
Alternative Decarbamoylation of N-Carbamoyl-L-Allo-Isoleucine Using Nitrous Acid The procedure of Example 7 is repeated except that N-carbamoyl-L-allo-isoleucine is used in place of N-carbamoyl-D-allo-isoleucine.

The preceding description has been presented with reference to presently preferred embodiments of the invention. Workers skilled in the art and technology to which this invention pertains will appreciate that alterations and changes in the described methods may be practiced without meaningfully departing from the principal, spirit and scope of this invention. Accordingly, the foregoing description should not be read as pertaining only to the precise methods described, but rather should be read consistent with and as support to the following claims which are to have their fullest and fair scope.

What is claimed is:

1. A method for producing D-allo-isoleucine comprising:
   converting (S)-2-methylbutyraldehyde to produce a hydantoin mixture containing a mixture of L-isoleucine hydantoin and D-allo-isoleucine hydantoin under conditions whereby no significant racemization of 2-methylbutyraldehyde occurs;
   contacting said hydantoin mixture with a D-hydantoinase to stereoselectively hydrolyze any D-allo-isoleucine hydantoin in the mixture to the corresponding N-carbamoyl-D-allo-isoleucine; and
   decarbamoylating the N-carbamoyl-D-allo-isoleucine to produce D-allo-isoleucine.

2. The method of claim 1, wherein the contacting of the hydantoin with a D-hydantoinase is carried out under conditions permitting the simultaneous epimerization of the chiral center at C-5 of the hydantoin.

3. The method of claim 2, wherein the simultaneous epimerization of the chiral center at C-5 of the hydantoin is carried out at a pH of about 7.5 or higher.

4. The method of claim 2, wherein the simultaneous epimerization of the chiral center at C-5 of the hydantoin is carried out at a pH ranging from about 8.0 to about 9.5.

5. The method of claim 2, wherein at least about 75% of the L-isoleucine and D-allo-isoleucine hydantoins in the hydantoin mixture are converted to N-carbamoyl-D-allo-isoleucine.

6. The method of claim 2, wherein at least about 85% of the L-isoleucine and D-allo-isoleucine hydantoins in the hydantoin mixture are converted to N-carbamoyl-D-allo-isoleucine.

7. The method of claim 2, wherein at least about 95% of the L-isoleucine and D-allo-isoleucine hydantoins in the hydantoin mixture are converted to N-carbamoyl-D-allo-isoleucine.

8. The method of claim 1, wherein the decarbamoylation is carried out using a carbamoylase enzyme.

9. A method for producing D-isoleucine comprising:
   converting (R)-2-methylbutyraldehyde to produce a hydantoin mixture containing a mixture of D-isoleucine hydantoin and L-allo-isoleucine hydantoin under conditions whereby no significant racemization of 2-methylbutyraldehyde occurs;
   contacting said hydantoin mixture with a D-hydantoinase to stereoselectively hydrolyze any D-isoleucine hydantoin in the mixture to the corresponding N-carbamoyl-D-isoleucine; and
   decarbamoylating the N-carbamoyl-D-isoleucine to produce D-isoleucine.

10. The method of claim 9, wherein the contacting of the hydantoin with a D-hydantoinase is carried out under conditions permitting the simultaneous epimerization of the chiral center at C-5 of the hydantoin.

11. The method of claim 10, wherein the simultaneous epimerization of the chiral center at C-5 of the hydantoin is carried out at a pH of about 7.5 or higher.

12. The method of claim 10, wherein the simultaneous epimerization of the chiral center at C-5 of the hydantoin is carried out at a pH ranging from about 8.0 to about 9.5.

13. The method of claim 10, wherein at least about 75% of the D-isoleucine and L-allo-isoleucine hydantoins in the hydantoin mixture are converted to N-carbamoyl-D-isoleucine.

14. The method of claim 10, wherein at least about 85% of the D-isoleucine and L-allo-isoleucine hydantoins in the hydantoin mixture are converted to N-carbamoyl-D-isoleucine.

15. The method of claim 10, wherein at least about 95% of the D-isoleucine and L-allo-isoleucine hydantoins in the hydantoin mixture are converted to N-carbamoyl-D-isoleucine.

16. The method of claim 9, wherein the decarbamoylation is carried out using a carbamoylase enzyme.

17. A method for producing L-allo-isoleucine comprising:
converting (R)-2-methylbutyraldehyde to produce a hydantoin mixture containing a mixture of D-isoleucine hydantoin and L-allo-isoleucine hydantoin under conditions whereby no significant racemization of 2-methylbutyraldehyde occurs;
contacting said hydantoin mixture with an L-hydantoinase to stereoselectively hydrolyze any L-allo-isoleucine hydantoin in the mixture to the corresponding N-carbamoyl-L-allo-isoleucine; and
decarbamoylating the N-carbamoyl-L-allo-isoleucine to produce L-allo-isoleucine.

18. The method of claim 17, wherein the contacting of the hydantoin with an L-hydantoinase is carried out under conditions permitting the simultaneous epimerization of the chiral center at C-5 of the hydantoin.

19. The method of claim 18, wherein the simultaneous epimerization of the chiral center at C-5 of the hydantoin is carried out at a pH of about 7.5 or higher.

20. The method of claim 18, wherein the simultaneous epimerization of the chiral center at C-5 of the hydantoin is carried out at a pH ranging from about 8.0 to about 9.5.

21. The method of claim 18, wherein at least about 75% of the D-isoleucine and L-allo-isoleucine hydantoins in the hydantoin mixture are converted to N-carbamoyl-L-allo-isoleucine.

22. The method of claim 18, wherein at least about 85% of the D-isoleucine and L-allo-isoleucine hydantoins in the hydantoin mixture are converted to N-carbamoyl-L-allo-isoleucine.

23. The method of claim 18, wherein at least about 95% of the D-isoleucine and L-allo-isoleucine hydantoins in the hydantoin mixture are converted to N-carbamoyl-L-allo-isoleucine.

24. The method of claim 17, wherein the decarbamoylation is carried out using a carbamoylase enzyme.

25. A method for producing L-isoleucine comprising:
converting (S)-2-methylbutyraldehyde to produce a hydantoin mixture containing a mixture of D-allo-isoleucine hydantoin and L-isoleucine hydantoin under conditions whereby no significant racemization of 2-methylbutyraldehyde occurs;
contacting said hydantoin mixture with an L-hydantoinase to stereoselectively hydrolyze any L-isoleucine hydantoin in the mixture to the corresponding N-carbamoyl-L-isoleucine; and
decarbamoylating the N-carbamoyl-L-isoleucine to produce L-isoleucine.

26. The method of claim 25, wherein the contacting of the hydantoin with an L-hydantoinase is carried out under conditions permitting the simultaneous epimerization of the chiral center at C-5 of the hydantoin.

27. The method of claim 26, wherein the simultaneous epimerization of the chiral center at C-5 of the hydantoin is carried out at a pH of about 7.5 or higher.

28. The method of claim 26, wherein the simultaneous epimerization of the chiral center at C-5 of the hydantoin is carried out at a pH ranging from about 8.0 to about 9.5.

29. The method of claim 26, wherein at least about 75% of the D-allo-isoleucine and L-isoleucine hydantoins in the hydantoin mixture are converted to N-carbamoyl-L-isoleucine.

30. The method of claim 26, wherein at least about 85% of the D-allo-isoleucine and L-isoleucine hydantoins in the hydantoin mixture are converted to N-carbamoyl-L-isoleucine.

31. The method of claim 26, wherein at least about 95% of the D-allo-isoleucine and L-isoleucine hydantoins in the hydantoin mixture are converted to N-carbamoyl-L-isoleucine.

32. The method of claim 25, wherein the decarbamoylation is carried out using a carbamoylase enzyme.

33. A method for producing N-carbamoyl-D-allo-isoleucine comprising:
converting (S)-2-methylbutyraldehyde to a hydantoin mixture comprising L-isoleucine hydantoin and D-allo-isoleucine hydantoin under conditions in which no significant racemization of 2-methylbutyraldehyde occurs;
contacting said hydantoin mixture containing with a D-hydantoinase to stereoselectively hydrolyze D-allo-isoleucine hydantoin in the mixture to the corresponding N-carbamoyl-D-allo-isoleucine.

34. The method of claim 33, wherein the contacting of the hydantoin with a D-hydantoinase is carried out under conditions permitting the simultaneous epimerization of the chiral center at C-5 of the hydantoin.

35. The method of claim 34, wherein the simultaneous epimerization of the chiral center at C-5 of the hydantoin is carried out at a pH of about 7.5 or higher.

36. The method of claim 34, wherein the simultaneous epimerization of the chiral center at C-5 of the hydantoin is carried out at a pH ranging from about 8.0 to about 9.5.

37. The method of claim 34, wherein at least about 75% of the L-isoleucine and D-allo-isoleucine hydantoins in the hydantoin mixture are converted to N-carbamoyl-D-allo-isoleucine.

38. The method of claim 34, wherein at least about 85% of the L-isoleucine and D-allo-isoleucine hydantoins in the hydantoin mixture are converted to N-carbamoyl-D-allo-isoleucine.

39. The method of claim 34, wherein at least about 95% of the L-isoleucine and D-allo-isoleucine hydantoins in the hydantoin mixture are converted to N-carbamoyl-D-allo-isoleucine.

40. A method for producing N-carbamoyl-D-isoleucine comprising:
converting (R)-2-methylbutyraldehyde to a hydantoin mixture comprising D-isoleucine hydantoin and L-allo-isoleucine hydantoin under conditions in which no significant racemization of 2-methylbutyraldehyde occurs;
contacting said hydantoin mixture containing with a D-hydantoinase to stereoselectively hydrolyze D-isoleucine hydantoin in the mixture to the corresponding N-carbamoyl-D-isoleucine.

41. The method of claim 40, wherein the contacting of the hydantoin with a D-hydantoinase is carried out under conditions permitting the simultaneous epimerization of the chiral center at C-5 of the hydantoin.

42. The method of claim 41, wherein the simultaneous epimerization of the chiral center at C-5 of the hydantoin is carried out at a pH of about 7.5 or higher.

43. The method of claim 41, wherein the simultaneous epimerization of the chiral center at C-5 of the hydantoin is carried out at a pH ranging from about 8.0 to about 9.5.

44. The method of claim 41, wherein at least about 75% of the D-isoleucine and L-allo-isoleucine hydantoins in the hydantoin mixture are converted to N-carbamoyl-D-isoleucine.

45. The method of claim 41, wherein at least about 85% of the D-isoleucine and L-allo-isoleucine hydantoins in the hydantoin mixture are converted to N-carbamoyl-D-isoleucine.

46. The method of claim 41, wherein at least about 95% of the D-isoleucine and L-allo-isoleucine hydantoins in the hydantoin mixture are converted to N-carbamoyl-D-isoleucine.

47. A method for producing N-carbamoyl-L-allo-isoleucine comprising:

converting (R)-2-methylbutyraldehyde to a hydantoin mixture comprising D-isoleucine hydantoin and L-allo-isoleucine hydantoin under conditions in which no significant racemization of 2-methylbutyraldehyde occurs;

contacting said hydantoin mixture containing with an L-hydantoinase to stereoselectively hydrolyze L-allo-isoleucine hydantoin in the mixture to the corresponding N-carbamoyl-L-allo-isoleucine.

48. The method of claim 47, wherein the contacting of the hydantoin with an L-hydantoinase is carried out under conditions permitting the simultaneous epimerization of the chiral center at C-5 of the hydantoin.

49. The method of claim 47, wherein the simultaneous epimerization of the chiral center at C-5 of the hydantoin is carried out at a pH of about 7.5 or higher.

50. The method of claim 47, wherein the simultaneous epimerization of the chiral center at C-5 of the hydantoin is carried out at a pH ranging from about 8.0 to about 9.5.

51. The method of claim 47, wherein at least about 75% of the D-isoleucine and L-allo-isoleucine hydantoins in the hydantoin mixture are converted to N-carbamoyl-L-allo-isoleucine.

52. The method of claim 47, wherein at least about 85% of the D-isoleucine and L-allo-isoleucine hydantoins in the hydantoin mixture are converted to N-carbamoyl-L-allo-isoleucine.

53. The method of claim 47, wherein at least about 95% of the D-isoleucine and L-allo-isoleucine hydantoins in the hydantoin mixture are converted to N-carbamoyl-L-allo-isoleucine.

54. A method for producing N-carbamoyl-D-allo-isoleucine comprising:

converting (S)-2-methylbutyraldehyde to a hydantoin mixture comprising L-isoleucine hydantoin and D-allo-isoleucine hydantoin under conditions in which no significant racemization of 2-methylbutyraldehyde occurs;

contacting said hydantoin mixture containing with an L-hydantoinase to stereoselectively hydrolyze L-isoleucine hydantoin in the mixture to the corresponding N-carbamoyl-L-isoleucine.

55. The method of claim 54, wherein the contacting of the hydantoin with an L-hydantoinase is carried out under conditions permitting the simultaneous epimerization of the chiral center at C-5 of the hydantoin.

56. The method of claim 54, wherein the simultaneous epimerization of the chiral center at C-5 of the hydantoin is carried out at a pH of about 7.5 or higher.

57. The method of claim 54, wherein the simultaneous epimerization of the chiral center at C-5 of the hydantoin is carried out at a pH ranging from about 8.0 to about 9.5.

58. The method of claim 54, wherein at least about 75% of the L-isoleucine and D-allo-isoleucine hydantoins in the hydantoin mixture are converted to N-carbamoyl-L-isoleucine.

59. The method of claim 54, wherein at least about 85% of the L-isoleucine and D-allo-isoleucine hydantoins in the hydantoin mixture are converted to N-carbamoyl-L-isoleucine.

60. The method of claim 54, wherein at least about 95% of the L-isoleucine and D-allo-isoleucine hydantoins in the hydantoin mixture are converted to N-carbamoyl-L-isoleucine.

* * * * *

UNITED STATES PATENT AND TRADEMARK OFFICE
CERTIFICATE OF CORRECTION

PATENT NO. : 6,830,904 B2
DATED : December 14, 2004
INVENTOR(S) : Rozzell, Jr. et al.

It is certified that error appears in the above-identified patent and that said Letters Patent is hereby corrected as shown below:

<u>Title page,</u>
Item [56], References Cited, OTHER PUBLICATIONS,
"Williams, et al.," reference, delete "Barcelona Barcelona", insert
-- Barcelona, Barcelona --.

<u>Column 16,</u>
Lines 14 and 47, delete "containing".

<u>Column 17,</u>
Line 12, delete "containing".

<u>Column 18,</u>
Line 8, delete "containing".

Signed and Sealed this

Third Day of January, 2006

JON W. DUDAS
*Director of the United States Patent and Trademark Office*